United States Patent
Kobayashi et al.

(10) Patent No.: US 9,328,135 B2
(45) Date of Patent: May 3, 2016

(54) METHOD FOR PRODUCING POROUS SILK FIBROIN MATERIAL

(71) Applicants: Hitachi Chemical Company, Ltd., Tokyo (JP); National Institute of Agrobiological Sciences, Tsukuba-shi, Ibaraki (JP)

(72) Inventors: Kazutoshi Kobayashi, Tokyo (JP); Naosuke Sumi, Tokyo (JP); Tsuyoshi Abe, Tokyo (JP); Yasushi Tamada, Tokyo (JP)

(73) Assignees: Hitachi Chemical Company, Ltd., Tokyo (JP); National Institute of Agrobiological Sciences, Tsukuba-shi, Ibaraki (JP)

( * ) Notice: Subject to any disclaimer, the term of this patent is extended or adjusted under 35 U.S.C. 154(b) by 0 days.

(21) Appl. No.: 13/735,975

(22) Filed: Jan. 7, 2013

(65) Prior Publication Data

US 2013/0197193 A1     Aug. 1, 2013

Related U.S. Application Data

(63) Continuation of application No. 13/481,520, filed on May 25, 2012, now abandoned, which is a continuation of application No. 13/263,128, filed as application No. PCT/JP2010/056231 on Apr. 4, 2010, now abandoned.

(30) Foreign Application Priority Data

Apr. 6, 2009   (JP) ................................. 2009-092448

(51) Int. Cl.
C07K 1/02      (2006.01)
C07K 14/435    (2006.01)

(52) U.S. Cl.
CPC ............. *C07K 1/02* (2013.01); *C07K 14/43586* (2013.01)

(58) Field of Classification Search
None
See application file for complete search history.

(56) References Cited

U.S. PATENT DOCUMENTS

| | | | |
|---|---|---|---|
| 5,263,983 A | 11/1993 | Yoshizato et al. | |
| 2002/0114919 A1 | 8/2002 | Yoneda et al. | |

FOREIGN PATENT DOCUMENTS

| | | | |
|---|---|---|---|
| JP | 1-118544 | | 5/1989 |
| JP | 1-118652 | | 5/1989 |
| JP | 2-34171 | | 2/1990 |
| JP | 06-116810 | | 4/1994 |
| JP | 8-41097 | | 2/1996 |
| JP | 2002-186847 | | 7/2002 |
| JP | 2006-249115 | | 9/2006 |
| JP | 2008-255298 A | | 10/2008 |
| WO | WO 2007/020449 | * | 2/2007 |

OTHER PUBLICATIONS

Definition of "solution"—Retrieved Oct. 7, 2014 from < http://chemistry.about.com/od/chemistryglossary/a/solutiondef.htm >.*
Extended European Search Report dated Apr. 8, 2013, including European Search Opinion and Supplementary European Search Report, for EP Application No. 10761693.0-1410/2418239 (PCT/JP2010/056231).
Q. Lu, et al., "Preparation of 3-D regenerated fibroin scaffolds with freeze drying method and freeze drying/foaming technique", *J Mater Sci: Mater Med*, (2006), vol. 17, pp. 1349-1356.
W. Tao, et al., "Structure and properties of regenerated *Antheraea pernyi* silk fibroin in aqueous solution", *International Journal of Biological Macromolecules*, (2007), vol. 40, pp. 472-478.
E. Marsano, et al., "Wet spinning of *Bombyx mori* silk fibroin dissolved in N-methyl morpholine N-oxide and properties of regenerated fibres", *International Journal of Biological Macromolecules*, (2005), vol. 37, pp. 179-188.
Taiwanese Official Action dated Jun. 25, 2014, for TW Application No. 099110670.

* cited by examiner

*Primary Examiner* — Suzanne M Noakes
(74) *Attorney, Agent, or Firm* — Fitch, Even, Tabin & Flannery, LLP

(57) ABSTRACT

A method for producing a porous silk fibroin material, containing steps of: freezing a silk fibroin solution containing a silk fibroin aqueous solution having an aliphatic carboxylic acid added thereto; and then melting the frozen solution, thereby providing a porous material. A method for producing a porous silk fibroin material having excellent mechanical characteristics may be provided.

13 Claims, 14 Drawing Sheets

METHOD FOR PRODUCING POROUS SILK FIBROIN MATERIAL

This application is a Continuation application of application Ser. No. 13/481,520, filed May 25, 2012, which is a Continuation application of application Ser. No. 13/263,128, filed Oct. 6, 2011, which is a National Stage application of International (PCT) Application No. PCT/JP2010/056231, filed Apr. 4, 2010, the contents of Ser. No. 13/263,128 being incorporated herein by reference in their entirety.

TECHNICAL FIELD

The present invention relates to a method for producing a porous silk fibroin material.

BACKGROUND ART

A porous material that can be produced with a biological material, such as a protein and a saccharide, is utilized in various fields in industries, for example, a medical field, such as a wound coverage, a hemostatic sponge and a pharmaceutical sustained-release carrier, daily goods, such as a disposable diaper and a sanitary napkin, a field of water purification where the porous material may be used as a support as a habitat of microorganisms and bacteria, a cosmetic and beauty treatment field aiming at moisture retention and the like by using the porous material personally or in an esthetic salon, and cell culture substrate and a tissue regeneration substrate in a tissue engineering and regeneration medical engineering.

As the biological material constituting the porous material, saccharides, such as cellulose and chitin, and proteins, such as collagen, keratin and silk fibroin, are known.

Among these, collagen has been most frequently used as a protein, but it is becoming difficult to use bovine collagen since the generation of BSE disaster. Keratin, which may be obtained from wool or feather, has a problem in availability of the raw materials thereof, and is difficult to use industrially. The raw materials of keratin is difficult to procure since wool is increased in raw material price, and feather has no market. Silk fibroin, on the other hand, may be utilized industrially since it is expected to be available stably from the standpoint of availability of raw materials, and is stable in price.

Silk fibroin has been used as surgical suture threads for a prolonged period of time in addition to the clothing purposes, and is also used currently as an additive for foods and cosmetics, owing to the safety for human body, and thus silk fibroin may be sufficiently utilized in the field of the porous material.

There has been several reports on a method for producing a porous silk fibroin material. In one method, for example, a silk fibroin aqueous solution is quickly frozen and then immersed in a crystallization solvent, thereby performing melting and crystallization simultaneously (Patent Document 1). In this method, however, an organic solvent as the crystallization solvent is necessarily used in a large amount, and the possible contamination with residual solvent may not be negated, which result in problems on the use in the application fields including the aforementioned medical field and the like. In another method, an aqueous solution of silk fibroin is gelled by maintaining the pH thereof at 6 or less or gelled by adding a poor solvent to the aqueous solution, and the resulting gel is freeze-dried, thereby providing a porous material (Patent Document 2). However, the method may not produce a porous material having sufficient strength. Furthermore, a method has been reported that a silk fibroin aqueous solution is frozen and then maintained in the frozen state for a long period of time, thereby providing a porous material (Patent Document 3). However, the investigations made by the present inventors reveal that the method is poor in reproducibility, and a porous material may frequently not be obtained.

A method that is reliable and convenient as compared to the aforementioned methods for producing a porous silk fibroin material has been reported (Patent Document 4 and Non-patent Document 1). In this method, a small amount of an organic solvent is added to a silk fibroin aqueous solution, which is then frozen for a prescribed period of time and then melted, thereby providing a porous silk fibroin material. In this method, the organic solvent used in a small amount is removed by a rinsing step using ultrapure water providing substantially no residual solvent, and the resulting porous material in a moistened state has higher strength and is excellent in shape stability as compared to the ordinary porous materials reported.

RELATED ART DOCUMENTS

Patent Documents

Patent Document 1: JP-A-8-41097
Patent Document 2: JP-B-6-94518
Patent Document 3: JP-A-2006-249115
Patent Document 4: Japanese Patent No. 3,412,014

Non-Patent Document

Non-patent Document 1: Biomacromolecules, vol. 6, pp. 3100-3106 (2005)

DISCLOSURE OF THE INVENTION

Depending on the field where the porous material is used and the method of using the porous material, the porous material produced by the method disclosed in Patent Document 4 may have insufficient strength in some cases, and there is a demand of increase of the strength.

An object of the present invention is to provide a method for producing a porous silk fibroin material that has excellent mechanical characteristics.

As a result of earnest investigations made by the present inventors, it has been found that a porous material having high strength is obtained by freezing a solution containing a silk fibroin aqueous solution having an aliphatic carboxylic acid added thereto, and then melting the frozen solution.

The present invention provides a method for producing a porous silk fibroin material, containing steps of: freezing a silk fibroin solution containing a silk fibroin aqueous solution having an aliphatic carboxylic acid added thereto; and then melting the frozen solution, thereby providing a porous material.

According to the present invention, a porous silk fibroin material having high strength is conveniently provided.

BEST MODE FOR CARRYING OUT THE INVENTION

Figure 1:
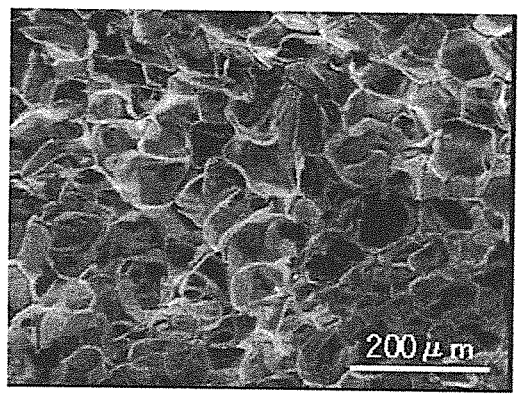
FIG. 1 The figure is a scanning electron micrograph showing an cross section of a porous silk fibroin material produced in Example 1.

The method for producing a porous silk fibroin material of the present invention contains steps of: freezing a silk fibroin solution containing a silk fibroin aqueous solution having an aliphatic carboxylic acid added thereto; and then melting the frozen solution, thereby providing a porous material.

The production method of the present invention preferably contains a step of removing the aliphatic carboxylic acid by immersing the porous material obtained after melting in pure water or by freeze-drying the porous material.

The silk fibroin used in the present invention may be any material that is derived from a silk worm, such as a domesticated silkworm, a wild silkworm and a Yamamay silkworm, and the production method thereof is not limited. In the present invention, silk fibroin is used as a silk fibroin aqueous solution, but silk fibroin is poor in solubility and thus is difficult to dissolve directly in water. As a method for providing the silk fibroin aqueous solution, any known method may be used, and such a method may be conveniently employed that silk fibroin is dissolved in a lithium bromide aqueous solution having a high concentration, and is then desalinated through dialysis and concentrated through air drying.

In the method for producing a porous silk fibroin material of the present invention, the concentration of the silk fibroin is preferably from 0.1 to 40% by mass, more preferably from 0.5 to 20% by mass, and further preferably from 1.0 to 12% by mass, in the silk fibroin solution having the aliphatic carboxylic acid added thereto. When the concentration is in the range, a porous material having sufficient strength may be produced efficiently.

In the present invention the aliphatic carboxylic acid added to the silk fibroin aqueous solution is not particularly limited and is preferably a water-soluble one, and more preferably one having a high solubility in water. The aliphatic carboxylic acid used in the present invention preferably has pKa of 5.0 or less, more preferably from 3.0 to 5.0, and further preferably from 3.5 to 5.0.

Preferred examples of the aliphatic carboxylic acid used in the present invention include saturated or unsaturated, monocarboxylic, dicarboxylic or tricarboxylic acids having from 1 to 6 carbon atoms, and specific examples thereof include formic acid, acetic acid, propionic acid, butyric acid, succinic acid, lactic acid, acrylic acid, 2-butenoic acid and 3-butenoic acid. The aliphatic carboxylic acids may be used solely or as a combination of two or more kinds thereof.

The amount of the aliphatic carboxylic acid added to the silk fibroin aqueous solution is preferably from 0.01 to 18.0% by mass, and more preferably from 0.1 to 5.0% by mass, in the silk fibroin solution. When the amount is in the range, a porous material having sufficient strength may be produced.

In the production method of the present invention, the solution containing the silk fibroin aqueous solution having the aliphatic carboxylic acid added thereto is poured into a mold or a vessel, and placed in a low temperature thermostatic chamber to be frozen, and then melted, thereby producing a porous silk fibroin material.

The freezing temperature is not particularly limited as far as such it is a temperature that the silk fibroin aqueous solution having the aliphatic carboxylic acid added thereto is frozen, and is preferably approximately from −1 to −40° C., more preferably approximately from −5 to −40° C., and further preferably from −10 to −30° C.

The freezing time is preferably 2 hours or more, and more preferably 4 hours or more, for freezing sufficiently the silk fibroin aqueous solution having the aliphatic carboxylic acid added thereto, and maintaining the frozen state for a prescribed period of time.

The freezing method may be a method of decreasing the temperature of the silk fibroin aqueous solution having the aliphatic carboxylic acid added thereto constantly to the freezing temperature, and preferably such a method that the silk fibroin aqueous solution having the aliphatic carboxylic acid added thereto is once maintained at a temperature of approximately from 4 to −9° C., and preferably approximately from 0 to −5° C., for 30 minutes or more before freezing for making the interior of the reaction vessel homogeneous, and then frozen by decreasing the temperature thereof to the freezing temperature, for providing a porous silk fibroin material having a homogeneous structure. Furthermore, in the case where the temperature to be retained is approximately from −1 to −9° C., and preferably approximately from −1 to −5° C., the silk fibroin aqueous solution is at a temperature where the solution is in a supercooled state before freezing (i.e., the supercooling temperature), thereby providing a porous silk fibroin material having a more homogeneous structure. Moreover, the period of time of maintaining at the supercooling temperature may be controlled, or the temperature gradient upon decreasing the temperature from the supercooling temperature to the freezing temperature may be controlled, whereby a porous silk fibroin material having a further homogeneous structure may be obtained, and the structure and the strength of the porous material may be controlled to a certain extent.

Thereafter, the silk fibroin solution thus frozen is melted, thereby providing a porous silk fibroin material. The method of melting is not particularly limited, and examples thereof include spontaneous melting and storage in a thermostatic chamber.

The resulting porous material contains the aliphatic carboxylic acid, and the aliphatic carboxylic acid is necessarily removed, or the concentration thereof is necessarily controlled, depending on the purpose thereof. In this case, the aliphatic carboxylic acid contained in the porous silk fibroin material may be removed by a suitable method after producing the porous material, thereby controlling the concentration thereof. Specific examples of the most convenient method therefor include a method of immersing the porous material in pure water for performing dialysis.

Examples of the method of controlling the water concentration of the porous silk fibroin material after the production thereof include a method of evaporating water by drying the porous silk fibroin material. Examples of the drying method include spontaneous drying, freeze drying and heat drying, and freeze drying is preferred since contraction upon drying may be suppressed. The aliphatic carboxylic acid and water may be simultaneously removed by drying the porous material by freeze drying or the like.

The porous silk fibroin material obtained by the production method of the present invention may be formed into a shape corresponding to the purpose thereof, such as a film shape, a block shape and a tubular shape, by selecting appropriately the mold or the vessel upon used on producing the porous material.

The porous silk fibroin material obtained by the production method of the present invention has a sponge-like porous structure, and the porous material contains water, when water is not removed by freeze drying or the like, and is in the form of hard structure in a moistened state.

The size of the fine pores (i.e., the fine pore diameter) in the porous material obtained by the production method of the present invention is generally from 10 to 300 μm. The porous material may be freeze-dried to provide a dried material of the porous silk fibroin material.

The porous silk fibroin material obtained by the production method of the present invention has excellent mechanical characteristics. Specifically, the porous material has a larger tensile strength and a relatively larger elongation than porous materials that use methanol, ethanol, isopropanol, butanol, glycerol, dimethylsulfoxide (DMSO), dimethylformamide (DMF), pyridine, acetone or acetonitrile, which are the organic solvents used in Patent Document 4.

The porous fibroin material obtained by the production method of the present invention has high water absorbing property and involves no problem in safety, and thus may be applied widely to a cosmetic and beauty treatment field aiming at moisture retention and the like. Specifically, the porous material may be favorably used as a peeling pack and a cosmetic puff. The porous material in a desired shape may be easily obtained by changing the shape of the vessel used on freezing, and thus the porous material may be favorably used as a face mask that follows the shape of the face.

The weight of the porous fibroin material obtained by the production method of the present invention may be controlled by changing the water absorption amount thereof, and the porous material involves no problem in safety. Accordingly, the porous material may be favorably used as a weight for pulling a biological tissue excised under observation with an endoscope.

Furthermore, the porous fibroin material obtained by the production method of the present invention has high strength and high water absorbing property and involves no problem in safety, and thus may be favorably applied to a medical field, such as a wound coverage, a pharmaceutical sustained-release carrier and a hemostatic sponge, daily goods, such as a disposable diaper and a sanitary napkin, a cell culture substrate and a tissue regeneration substrate in tissue engineering and regeneration medical engineering, and a support as a habitat of microorganisms and bacteria in a field of water purification and environmental protection.

EXAMPLE

The present invention is described more specifically with reference to examples below, but the present invention is not limited to the examples.

Example 1

Preparation of Silk Fibroin Solution

A silk fibroin solution was obtained by dissolving fibroin powder ("Silkpowder IM", a trade name, produced by KB Seiren, Ltd.) in a 9M lithium bromide aqueous solution, removing insoluble matters through centrifugation, and performing repeatedly dialysis against pure water. The resulting silk fibroin solution was concentrated by air-drying in the dialysis tube. A formic acid aqueous solution was added to the concentrated solution, thereby preparing a silk fibroin solution having a silk fibroin concentration of 5% by mass and a formic acid concentration of 2% by mass.

Production of Porous Silk Fibroin Material

The silk fibroin solution was poured into a mold (inner dimension: 80 mm×40 mm×4 mm) produced with aluminum plates, and stored in a frozen state in a low temperature thermostat chamber (NCB-3300, produced by Tokyo Rikakikai Co., Ltd. (EYELA)).

Freezing Condition

Freezing was performed in the following manner. The silk fibroin solution in the mold was placed in the low temperature thermostat chamber, which had been cooled to −5° C. in advance, and maintained for 2 hours. Thereafter, the solution was cooled until the interior of the chamber reached −20° C. at a cooling rate of 3° C. per hour over 5 hours, and then maintained at −20° C. for 5 hours.

The frozen specimen was returned to room temperature through spontaneous melting, taken Out from the mold, and immersed in ultrapure water, and the ultrapure water was exchanged twice per one day over 3 days, thereby removing the formic acid used.

The resulting porous silk fibroin material was evaluated for mechanical characteristics with Microtester Model 5548, produced by Instron Japan Co., Ltd. A test piece of 40 mm×4 mm×4 mm was cut out from the porous silk fibroin material thus produced, and the test piece was measured for a tensile strength (maximum breaking strength) and a maximum (breaking) distortion (elongation) upon pulling under condition of 2 mm/min. The elastic modulus of the test piece was obtained from the gradient of the graph of the strength and the distortion. The results are shown in Table 1. The measurement result was an average value of measurement results of 10 test pieces, which were obtained by cutting out 5 test pieces from the porous material produced and separately cutting out another 5 test pieces from the porous material produced on another day.

The structure of the resulting porous silk fibroin material was observed with a scanning electron microscope. The scanning electron microscope used was XL30-FEG, produced by Philips Electronics, and the measurement was performed with the low vacuum and no deposition mode and an acceleration voltage of 10 kV. The structure of the porous silk fibroin material was observed for the interior thereof exposed by cutting the porous material, but not the surface of the porous material. The scanning electron micrograph of the cross section of the resulting porous material is shown in FIG. 1.

The resulting porous silk fibroin material was impregnated with water to the equilibrium state by immersing the porous material in ultrapure water, and then measured for wet weight (Wa). The porous material was then sufficiently dried by freeze drying, and the porous material was measured for dry weight (Wb). The water content of the porous material was calculated from these values according to the following equation. The results are described later.

$$\text{water content}(\%)=(Wa-Wb)\times 100/Wa$$

Example 2

Figure 2:
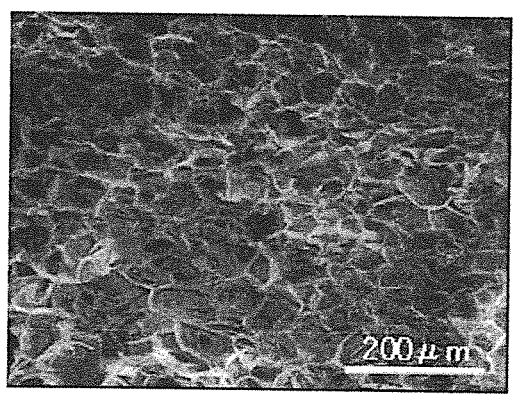
FIG. 2 The figure is a scanning electron micrograph showing an cross section of a porous silk fibroin material produced in Example 2.

A porous silk fibroin material was produced in the same manner as in Example 1 except that acetic acid was used instead of formic acid. The evaluation results for mechanical characteristics thereof are shown in Table 1. The scanning electron micrograph of the cross section of the resulting porous material is shown in FIG. 2.

Example 3

Figure 3:
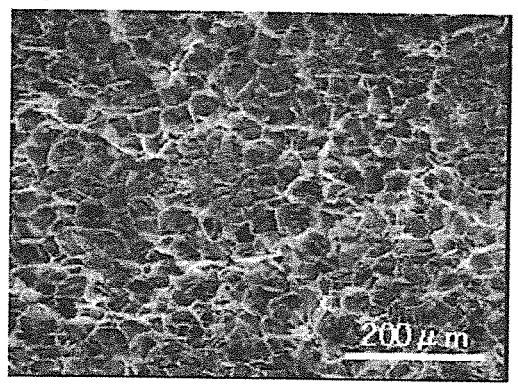
FIG. 3 The figure is a scanning electron micrograph showing an cross section of a porous silk fibroin material produced in Example 3.

A porous silk fibroin material was produced in the same manner as in Example 1 except that propionic acid was used instead of formic acid. The evaluation results for mechanical characteristics thereof are shown in Table 1. The scanning electron micrograph of the cross section of the resulting porous material is shown in FIG. 3.

Example 4

Figure 4:
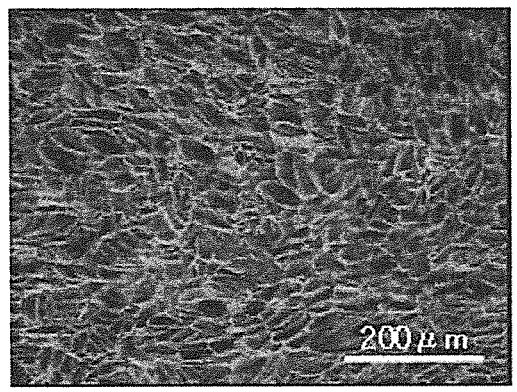
FIG. 4 The figure is a scanning electron micrograph showing an cross section of a porous silk fibroin material produced in Example 4.

A porous silk fibroin material was produced in the same manner as in Example 1 except that butyric acid was used instead of formic acid. The evaluation results for mechanical characteristics thereof are shown in Table 1. The scanning electron micrograph of the cross section of the resulting porous material is shown in FIG. 4.

Example 5

Figure 5:
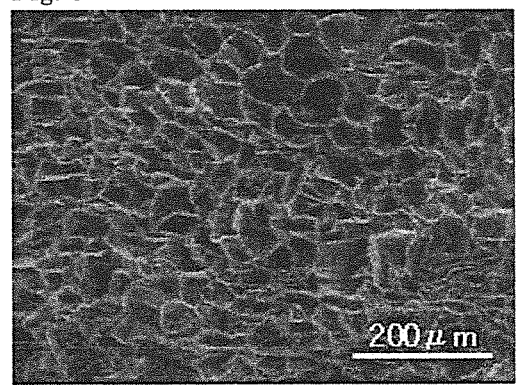
FIG. 5 The figure is a scanning electron micrograph showing an cross section of a porous silk fibroin material produced in Example 5.

A porous silk fibroin material was produced in the same manner as in Example 1 except that succinic acid was used instead of formic acid. The evaluation results for mechanical characteristics thereof are shown in Table 1. The scanning electron micrograph of the cross section of the resulting porous material is shown in FIG. 5.

Example 6

Figure 6:
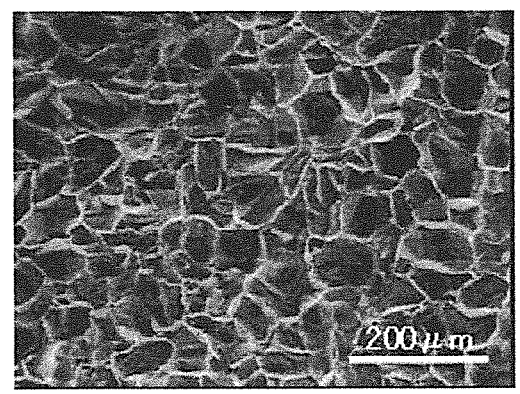
FIG. 6 The figure is a scanning electron micrograph showing an cross section of a porous silk fibroin material produced in Example 6.

A porous silk fibroin material was produced in the same manner as in Example 1 except that lactic acid was used instead of formic acid. The evaluation results for mechanical characteristics thereof are shown in Table 1. The scanning electron micrograph of the cross section of the resulting porous material is shown in FIG. 6.

Example 7

Figure 7:
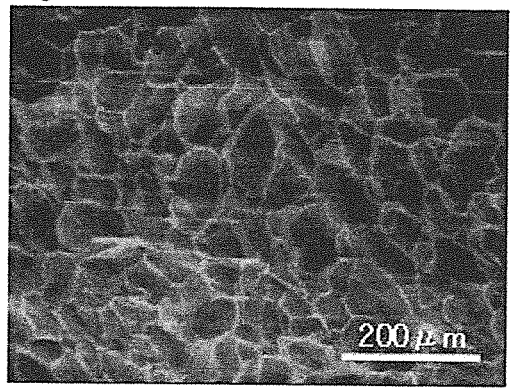
FIG. 7 The figure is a scanning electron micrograph showing an cross section of a porous silk fibroin material produced in Example 7.

A porous silk fibroin material was produced in the same manner as in Example 1 except that acrylic acid was used instead of formic acid. The evaluation results for mechanical characteristics thereof are shown in Table 1. The scanning electron micrograph of the cross section of the resulting porous material is shown in FIG. 7.

Example 8

Figure 8:
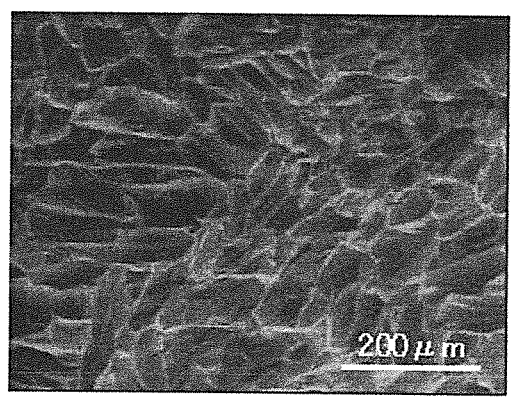
FIG. 8 The figure is a scanning electron micrograph showing an cross section of a porous silk fibroin material produced in Example 8.

A porous silk fibroin material was produced in the same manner as in Example 1 except that 2-butenoic acid was used instead of formic acid. The evaluation results for mechanical characteristics thereof are shown in Table 1. The scanning electron micrograph of the cross section of the resulting porous material is shown in FIG. 8.

Example 9

Figure 9:
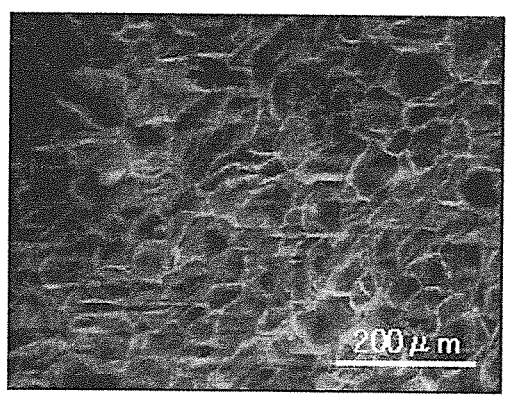
FIG. 9 The figure is a scanning electron micrograph showing an cross section of a porous silk fibroin material produced in Example 9.

A porous silk fibroin material was produced in the same manner as in Example 1 except that 3-butenoic acid was used instead of formic acid. The evaluation results for mechanical characteristics thereof are shown in Table 1. The scanning electron micrograph of the cross section of the resulting porous material is shown in FIG. 9.

Comparative Example 1

Figure 10:
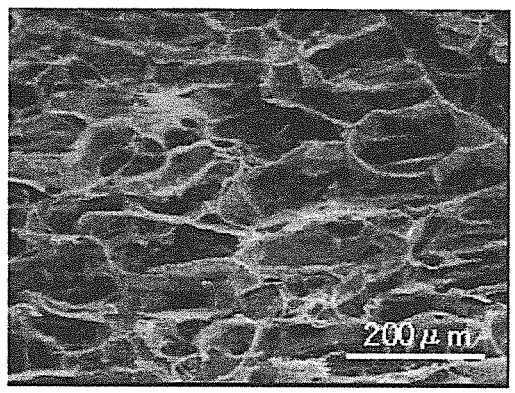
FIG. 10 The figure is a scanning electron micrograph showing an cross section of a porous silk fibroin material produced in Comparative Example 1.

A porous silk fibroin material was produced in the same manner as in Example 1 except that methanol was used instead of formic acid. The evaluation results for mechanical characteristics thereof are shown in Table 1. The scanning electron micrograph of the cross section of the resulting porous material is shown in FIG. 10.

Comparative Example 2

Figure 11:
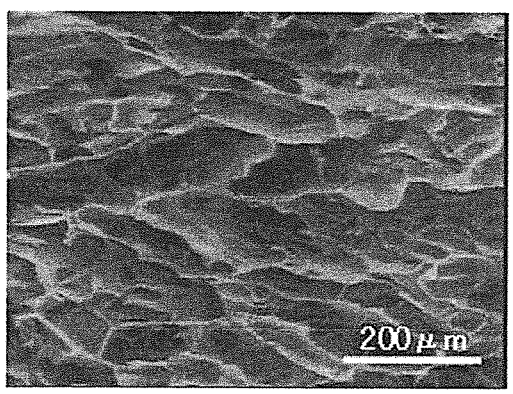
FIG. 11 The figure is a scanning electron micrograph showing an cross section of a porous silk fibroin material produced in Comparative Example 2.

A porous silk fibroin material was produced in the same manner as in Example 1 except that ethanol was used instead of formic acid. The evaluation results for mechanical characteristics thereof are shown in Table 1. The scanning electron micrograph of the cross section of the resulting porous material is shown in FIG. 11.

Comparative Example 3

Figure 12:
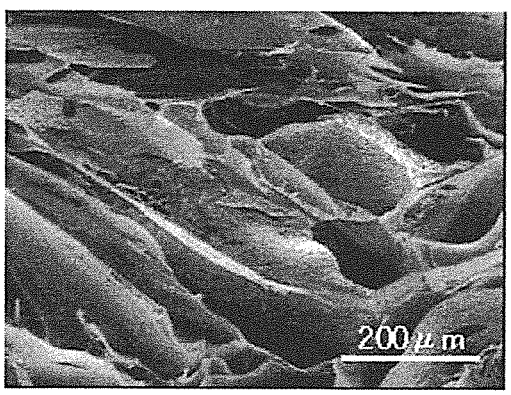
FIG. 12 The figure is a scanning electron micrograph showing an cross section of a porous silk fibroin material produced in Comparative Example 3.

A porous silk fibroin material was produced in the same manner as in Example 1 except that isopropanol was used instead of formic acid. The evaluation results for mechanical characteristics thereof are shown in Table 1. The scanning electron micrograph of the cross section of the resulting porous material is shown in FIG. 12.

Comparative Example 4

Figure 13:
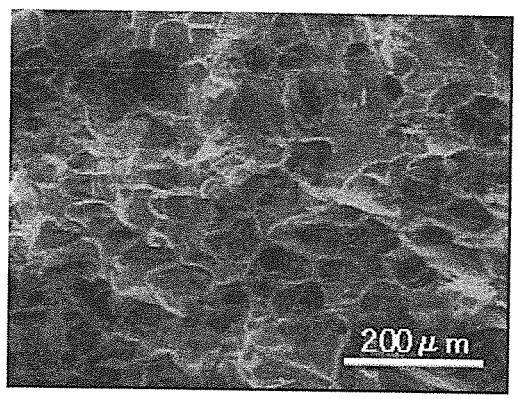
FIG. 13 The figure is a scanning electron micrograph showing an cross section of a porous silk fibroin material produced in Comparative Example 4.

A porous silk fibroin material was produced in the same manner as in Example 1 except that butanol was used instead of formic acid. The evaluation results for mechanical characteristics thereof are shown in Table 1. The scanning electron micrograph of the cross section of the resulting porous material is shown in FIG. 13.

Comparative Example 5

Figure 14:
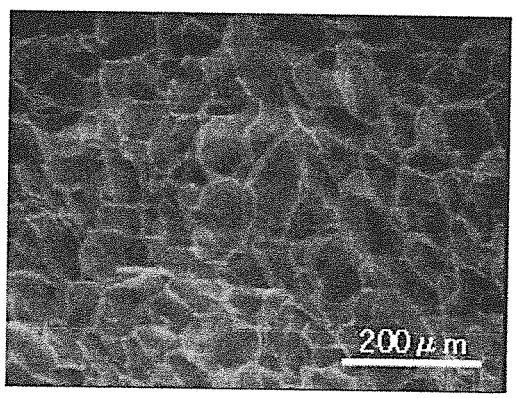
FIG. 14 The figure is a scanning electron micrograph showing an cross section of a porous silk fibroin material produced in Comparative Example 5.

A porous silk fibroin material was produced in the same manner as in Example 1 except that t-butanol was used instead of formic acid. The evaluation results for mechanical characteristics thereof are shown in Table 1. The scanning electron micrograph of the cross section of the resulting porous material is shown in FIG. 14.

Comparative Example 6

Figure 15:
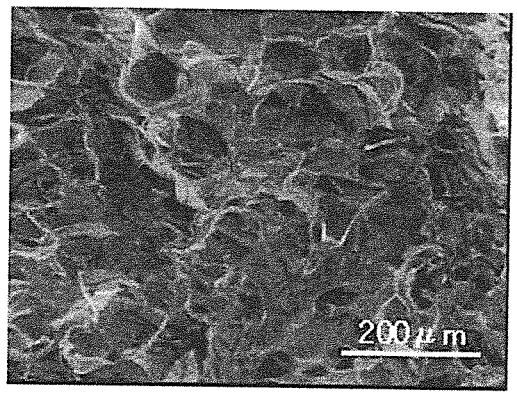
FIG. 15 The figure is a scanning electron micrograph showing an cross section of a porous silk fibroin material produced in Comparative Example 6.

A porous silk fibroin material was produced in the same manner as in Example 1 except that glycerol was used instead of formic acid. The evaluation results for mechanical characteristics thereof are shown in Table 1. The scanning electron micrograph of the cross section of the resulting porous material is shown in FIG. 15.

Comparative Example 7

Figure 16:
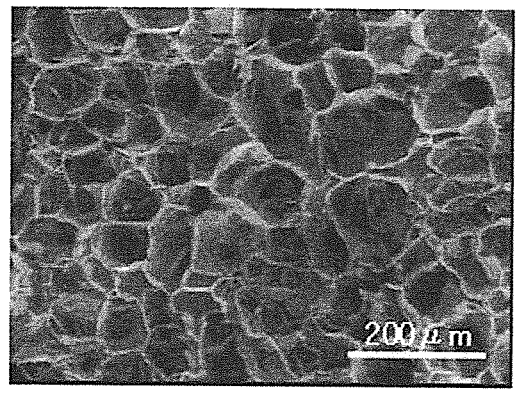
FIG. 16 The figure is a scanning electron micrograph showing an cross section of a porous silk fibroin material produced in Comparative Example 7.

A porous silk fibroin material was produced in the same manner as in Example 1 except that DMSO was used instead of formic acid. The evaluation results for mechanical characteristics thereof are shown in Table 1. The scanning electron micrograph of the cross section of the resulting porous material is shown in FIG. 16.

Comparative Example 8

Figure 17:
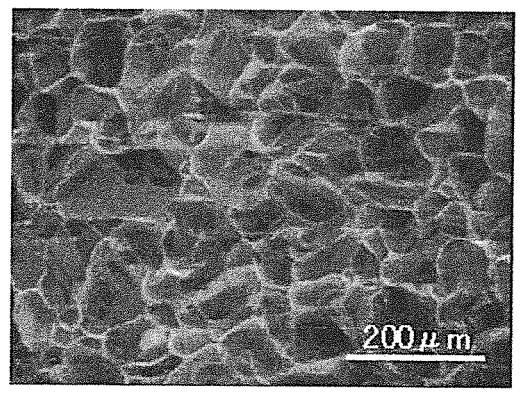
FIG. 17 The figure is a scanning electron micrograph showing an cross section of a porous silk fibroin material produced in Comparative Example 8.

A porous silk fibroin material was produced in the same manner as in Example 1 except that DMF was used instead of formic acid. The evaluation results for mechanical characteristics thereof are shown in Table 1. The scanning electron micrograph of the cross section of the resulting porous material is shown in FIG. 17.

Comparative Example 9

Figure 18:
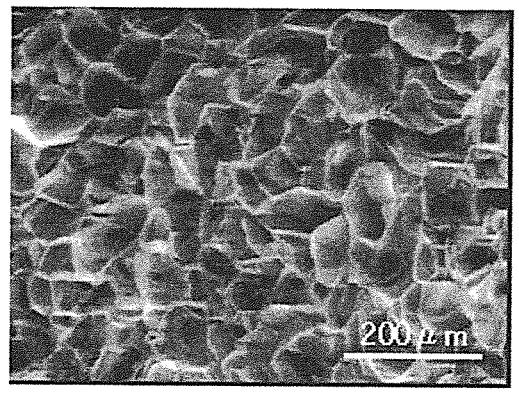
FIG. 18 The figure is a scanning electron micrograph showing an cross section of a porous silk fibroin material produced in Comparative Example 9

A porous silk fibroin material was produced in the same manner as in Example 1 except that pyridine was used instead of formic acid. The evaluation results for mechanical characteristics thereof are shown in Table 1. The scanning electron micrograph of the cross section of the resulting porous material is shown in FIG. 18.

Comparative Example 10

Figure 19:
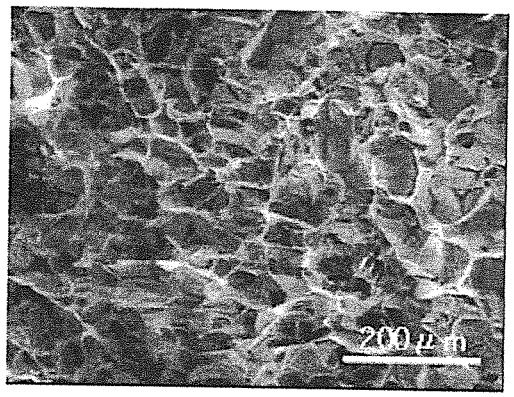
FIG. 19 The figure is a scanning electron micrograph showing an cross section of a porous silk fibroin material produced in Comparative Example 10.

A porous silk fibroin material was produced in the same manner as in Example 1 except that acetonitrile was used instead of formic acid. The evaluation results for mechanical characteristics thereof are shown in Table 1. The scanning electron micrograph of the cross section of the resulting porous material is shown in FIG. 19.

Comparative Example 11

Figure 20:
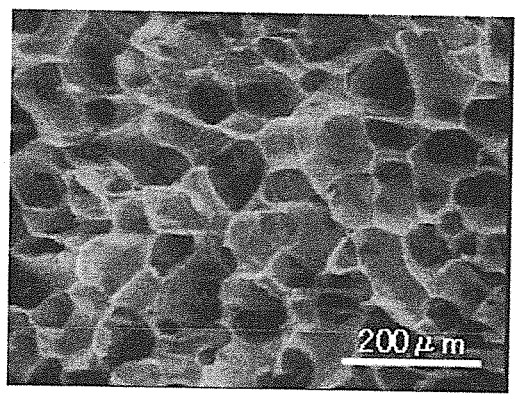
FIG. 20 The figure is a scanning electron micrograph showing an cross section of a porous silk fibroin material produced in Comparative Example 11.

A porous silk fibroin material was produced in the same manner as in Example 1 except that acetone was used instead of formic acid. The evaluation results for mechanical characteristics thereof are shown in Table 1. The scanning electron micrograph of the cross section of the resulting porous material is shown in FIG. 20.

Comparative Example 12

In Example 8 of Patent Document 2, an acetic acid solution is added to a silk fibroin aqueous solution to deposit a gelled product, and the resulting gel is freeze-dried to provide a porous material. No gel was formed in the trace experiment according to the disclosure, and a gelled product and a porous material were obtained under the following conditions.

Figure 21:
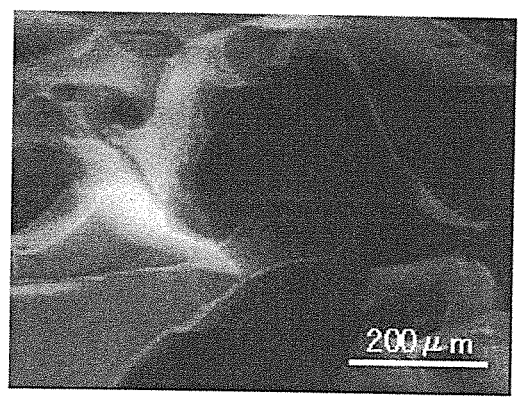
FIG. 21 The figure is a scanning electron micrograph showing an cross section of a porous silk fibroin material produced in Comparative Example 12.

130 mL of an acetic acid solution with pH 2.65 was added to 50 mL of a 5% silk fibroin aqueous solution (pH was 3.0 in this stage). The resulting solution was allowed to stand at 5° C. for 40 hours, and thus gel was formed. The resulting gel was centrifugally separated, and after removing the supernatant liquid, the gel was frozen at −30° C. for 3 hours and then freeze-dried for 50 hours, thereby providing a porous material. The evaluation results for mechanical characteristics of the porous material are shown in Table 1. The scanning electron micrograph of the cross section of the resulting porous material is shown in FIG. 21.

TABLE 1

|  | Organic compound added | Tensile strength (kPa) | Maximum distortion | Elastic modulus | pKa |
|---|---|---|---|---|---|
| Example 1 | formic acid | 80.9 | 0.64 | 203.6 | 3.77 |
| Example 2 | acetic acid | 118.9 | 0.76 | 290.4 | 4.56 |
| Example 3 | propionic acid | 98.0 | 0.70 | 229.3 | 4.67 |
| Example 4 | butyric acid | 145.7 | 0.53 | 287.3 | 4.63 |
| Example 5 | succinic acid | 101.6 | 0.54 | 158.8 | 4.00 |
| Example 6 | lactic acid | 116.8 | 0.59 | 189.6 | 3.66 |
| Example 7 | acrylic acid | 154.9 | 0.70 | 322.2 | 4.25 |
| Example 8 | 2-butenoic acid | 96.3 | 0.45 | 261.7 | 4.69 |
| Example 9 | 3-butenoic acid | 107.0 | 0.49 | 272.9 | 4.42 |
| Comparative Example 1 | methanol | 28.0 | 0.54 | 42.7 | 15.54 |
| Comparative Example 2 | ethanol | 29.1 | 0.21 | 175.6 | 16.0 |
| Comparative Example 3 | isopropanol | 14.3 | 0.36 | 26.8 | 16.5 |
| Comparative Example 4 | butanol | 57.3 | 0.39 | 141.9 | 16.1 |
| Comparative Example 5 | t-butanol | 39.1 | 0.30 | 93.3 | 18 |
| Comparative Example 6 | glycerol | 5.5 | 0.13 | 44.1 | 14.15 |
| Comparative Example 7 | DMSO | 42.6 | 0.53 | 86.4 | 35 |
| Comparative Example 8 | DMF | 66.2 | 0.64 | 192.6 | — |
| Comparative Example 9 | pyridine | 71.6 | 0.53 | 251.4 | 5.14 |
| Comparative Example 10 | acetonitrile | 72.4 | 0.53 | 180.2 | 25 |
| Comparative Example 11 | acetone | 72.6 | 0.52 | 234.1 | 20 |
| Comparative Example 12 | acetic acid | 5.5 | 0.07 | 0.06 | 4.56 |

It is understood from the results shown in Table 1 that the porous silk fibroin materials of Examples 1 to 9 using an aliphatic carboxylic acid each have a higher tensile strength than the porous silk fibroin materials of Comparative Examples 1 to 11 using methanol, ethanol, isopropanol, butanol, t-butanol, glycerol, DMSO, DMF, pyridine, acetonitrile and acetone, which are organic solvents used in Patent Document 4. The porous silk fibroin materials of Examples 1 to 9 each also have a larger maximum distortion (elongation). The porous silk fibroin materials of Examples 1 to 9 each exhibit a higher tensile strength as compared to Comparative Example 12.

According to FIG. 1, the porous silk fibroin material produced in Example 1 has a porous structure containing relatively thin walls and pores with several ten micrometers. The cross sections of the porous silk fibroin materials produced in Examples 2 to 9 (FIGS. 2 to 9) each provided the similar scanning electron micrograph.

The cross sections of the porous silk fibroin materials of Comparative Examples included (FIGS. 10 to 20) ones having the similar porous structure and ones having a layer structure, and there was no correlation observed between the structures and the mechanical characteristics. In Comparative Example 12, no distinct porous structure was observed.

It was found that the porous silk fibroin materials produced in Examples 1 to 9 each had a water content in a range of from 94 to 96%, which was substantially equivalent to the water contents of the porous materials produced in Comparative Examples 1 to 11. The porous material produced in Comparative Example 12 was considerably brittle and was not able to be calculated for water content.

Photosynthesis bacteria were cultured with the porous silk fibroin materials obtained in Examples as a culture base, and growth of the bacteria was confirmed.

Example 10

A porous fibroin material was produced in the same manner as in Example 1 except that acetic acid was used instead of formic acid, a mold having an inner dimension of 80 mm×40 mm×10 mm produced with aluminum plate was used, and the freezing condition was changed as follows. Acetic acid was removed from the resulting porous material in the same manner as described in Example 1.
Freezing Condition Freezing was performed in the following manner. The silk fibroin solution in the mold was placed in the low temperature thermostat chamber, which had been cooled to −1° C. in advance, and maintained for 0.5 hour. Thereafter, the solution was cooled until the interior of the chamber reached −20° C. at a cooling rate of 3° C. per hour over 6 hours and 20 minutes, and then maintained at −20° C. for 5 hours. The frozen specimen was returned to room temperature through spontaneous melting, and taken out from the mold, thereby providing a porous fibroin material. The porous fibroin material maintained the shape of the vessel used as a mold.

Figure 22:
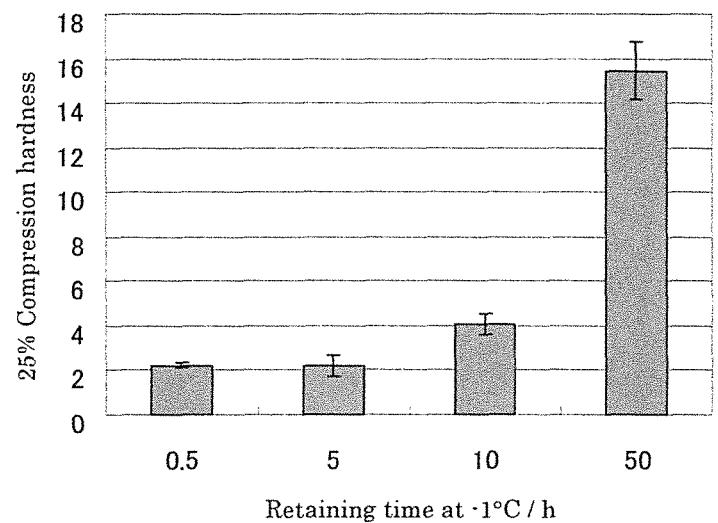
FIG. 22 The figure is a graph showing 25% compression hardness of porous silk fibroin materials produced in Examples 10 to 13.

The porous fibroin material was measured for 25% compression hardness in the following manner.
Measurement of 25% Compression Hardness by Compression Test The resulting porous fibroin material was completely impregnated with water by immersing in pure water for one day, and the hardness thereof was measured with a compression tester. The compression tester used was EZ Test, produced by Shimadzu Corporation, with load cells of 10 N and 50 N and a load plate with a diameter of 8 mm. The porous material was compressed to 25% of the initial thickness at a rate of 1 rum/min, and the load applied thereto was read and designated as the 25% compression hardness. The 25% compression hardness is shown in FIG. 22 and Table 2.

The measurement result was an average value (±standard deviation) of measurement results of 10 positions, which included arbitrary 5 positions of the porous material produced and arbitrary 5 positions of the porous material produced on another day.

Figure 23:
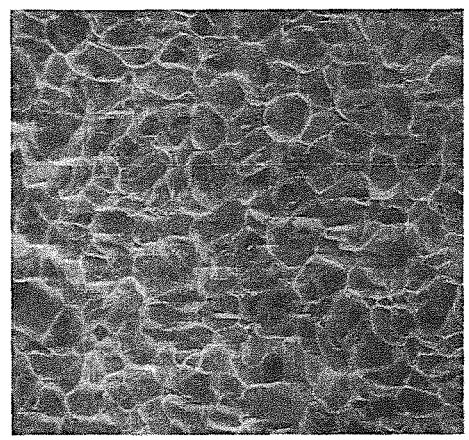
FIG. 23 The figure is a scanning electron micrograph showing an cross section of a porous silk fibroin material produced in Example 10.

The scanning electron micrograph of the cross section of the porous silk fibroin material is shown in FIG. 23.

Example 11

A porous silk fibroin material was produced in the same manner as in Example 10 except that the period of time where the temperature was maintained at −1° C. was changed from 0.5 hour to 5 hours. The 25% compression hardness of the resulting porous material is shown in FIG. 22 and Table 2.

Example 12

Figure 24:
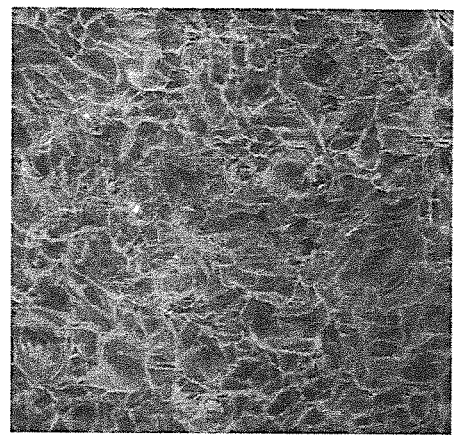
FIG. 24 The figure is a scanning electron micrograph showing an cross section of a porous silk fibroin material produced in Example 12.

A porous silk fibroin material was produced in the same manner as in Example 10 except that the period of time where the temperature was maintained at −1° C. was changed from 0.5 hour to 10 hours. The 25% compression hardness of the resulting porous material is shown in FIG. 22 and Table 2. The scanning electron micrograph of the cross section of the porous fibroin material is shown in FIG. 24.

Example 13

A porous silk fibroin material was produced in the same manner as in Example 10 except that the period of time where the temperature was maintained at −1° C. was changed from 0.5 hour to 50 hours. The 25% compression hardness of the resulting porous material is shown in FIG. 22 and Table 2.

TABLE 2

| Example | 10 | 11 | 12 | 13 |
|---|---|---|---|---|
| Pre-cooling time (h) | 0.5 | 5 | 10 | 50 |
| 25% compression hardness (N) | 2.22 (±0.103) | 2.19 (+0.492) | 4.05 (±0.482) | 15.4 (±1.311) |

Example 14

Figure 25:
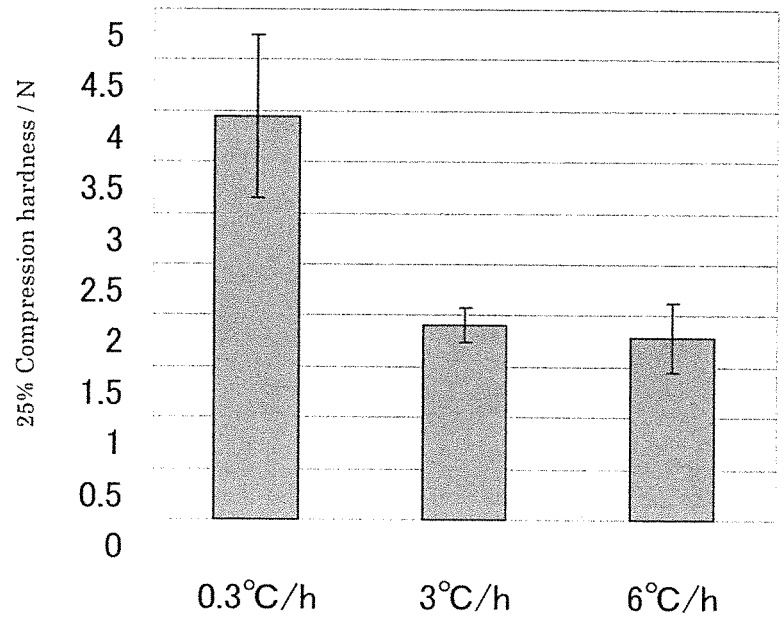
FIG. 25 The figure is a graph showing 25% compression hardness of porous silk fibroin materials produced in Examples 14 to 16.
Figure 26:
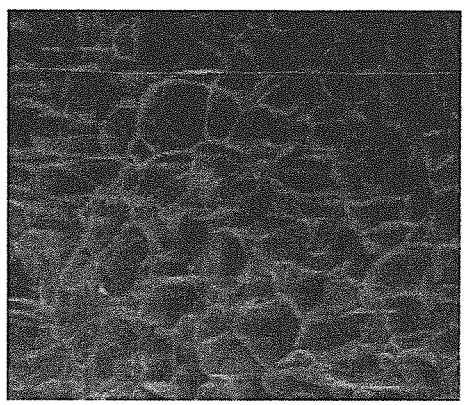
FIG. 26 The figure is a scanning electron micrograph showing an cross section of a porous silk fibroin material produced in Example 14.

A porous silk fibroin material was produced in the same manner as in Example 10 except that the freezing condition was changed as follows. The 25% compression hardness of the resulting porous material is shown in FIG. 25 and Table 3. The scanning electron micrograph of the cross section of the porous silk fibroin material is shown in FIG. 26.

Freezing Condition

Freezing was performed in the following manner. The silk fibroin solution in the mold was placed in the low temperature thermostat chamber, which had been cooled to −5° C. in advance, and maintained for 2 hours. Thereafter, the solution was cooled until the interior of the chamber reached −20° C. at a cooling rate of 0.3° C. per hour over 50 hours, and then maintained at −20° C. for 5 hours. The frozen specimen was returned to room temperature through spontaneous melting, and taken out from the mold, thereby providing a porous silk fibroin material. The porous silk fibroin material maintained the shape of the vessel used as a mold.

Example 15

Figure 27:
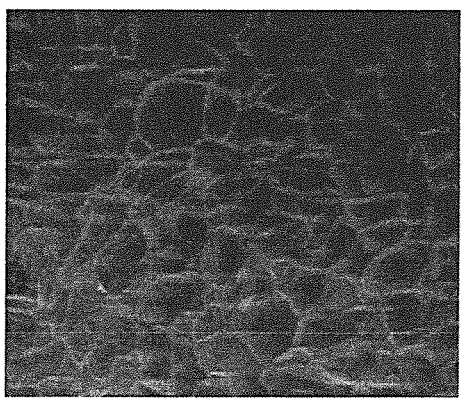
FIG. 27 The figure is a scanning electron micrograph showing an cross section of a porous silk fibroin material produced in Example 15.

A porous silk fibroin material was produced in the same manner as in Example 14 except that the cooling rate from −5° C. to −20° C. was changed to 3° C. per hour, and the cooling time thereover was changed to 5 hours. The 25% compression hardness of the resulting porous material is shown in FIG. 25 and Table 3. The scanning electron micrograph of the cross section of the porous silk fibroin material is shown in FIG. 27.

Example 16

Figure 28:
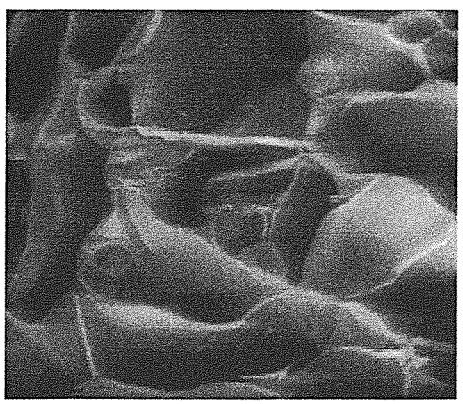
FIG. 28 The figure is a scanning electron micrograph showing an cross section of a porous silk fibroin material produced in Example 16.

A porous silk fibroin material was produced in the same manner as in Example 14 except that the cooling rate from −5° C. to −20° C. was changed to 6° C. per hour, and the cooling time thereover was changed to 2.5 hours. The 25% compression hardness of the resulting porous material is shown in FIG. 25 and Table 3. The scanning electron micrograph of the cross section of the porous silk fibroin material is shown in FIG. 28.

TABLE 3

| Example | 14 | 15 | 16 |
|---|---|---|---|
| Cooling rate (° C. per hour) | 0.3° C. per hour | 3° C. per hour | 6° C. per hour |
| 25% compression hardness (N) | 3.95 (±0.804) | 1.91 (±0.170) | 1.79 (±0.347) |

As shown by Examples 10 to 16, the strength of the resulting porous silk fibroin material may be controlled by controlling the freezing condition in the production method of the present invention.

Example 17

Figure 29:
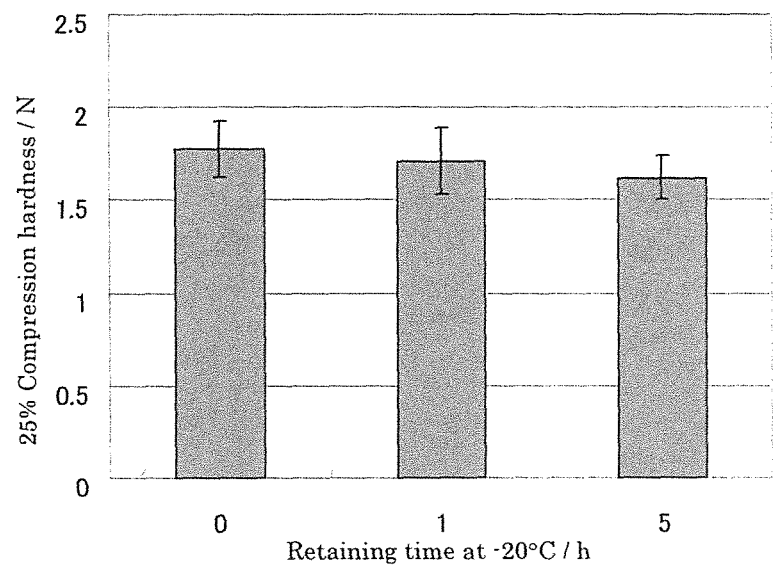
FIG. 29 The figure is a graph showing 25% compression hardness of porous silk fibroin materials produced in Examples 17 to 19.
Figure 30:
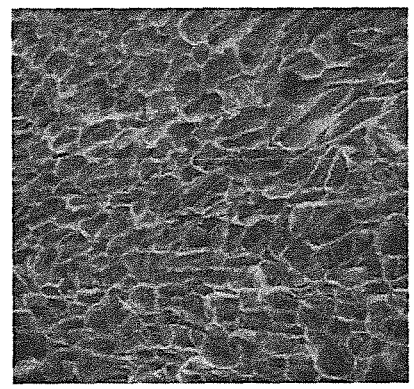
FIG. 30 The figure is a scanning electron micrograph showing an cross section of a porous silk fibroin material produced in Example 17.

A porous silk fibroin material was produced in the same manner as in Example 10 except that the freezing condition was changed as follows. The 25% compression hardness of the resulting porous material is shown in FIG. 29 and Table 4. The scanning electron micrograph of the cross section of the porous silk fibroin material is shown in FIG. 30.

Freezing Condition

Freezing was performed in the following manner. The silk fibroin solution in the mold was placed in the low temperature thermostat chamber, which had been cooled to −1° C. in advance, and maintained for 2 hours. Thereafter, the solution was cooled until the interior of the chamber reached −20° C. at a cooling rate of 3° C. per hour over 6 hours and 20 minutes, and immediately melted by increasing the temperature at 8° C. per hour.

Example 18

Figure 31:
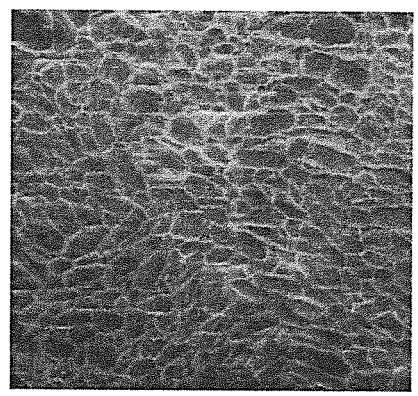
FIG. 31 The figure is a scanning electron micrograph showing an cross section of a porous silk fibroin material produced in Example 18.

A porous silk fibroin material was produced in the same manner as in Example 17 except that the silk fibroin solution was cooled until the interior of the chamber reached −20° C. and maintained at −20° C. for 1 hour (i.e., the period of time where the temperature was maintained at −20° C. was changed from 0 hour to 1 hour). The 25% compression hardness of the resulting porous material is shown in FIG. 29 and Table 4. The scanning electron micrograph of the cross section of the porous silk fibroin material is shown in FIG. 31.

Example 19

Figure 32:
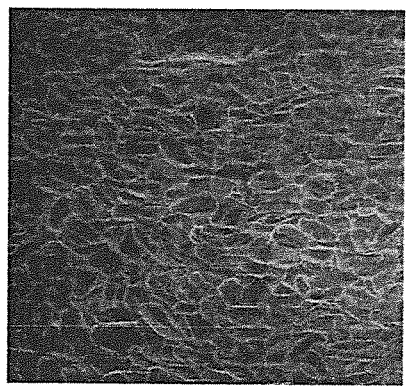
FIG. 32 The figure is a scanning electron micrograph showing an cross section of a porous silk fibroin material produced in Example 19.

A porous silk fibroin material was produced in the same manner as in Example 17 except that the silk fibroin solution was cooled until the interior of the chamber reached −20° C. and maintained at −20° C. for 5 hours (i.e., the period of time where the temperature was maintained at −20° C. was changed from 0 hour to 5 hours). The 25% compression hardness of the resulting porous material is shown in FIG. 29 and Table 4. The scanning electron micrograph of the cross section of the resulting porous silk fibroin material is shown in FIG. 32.

TABLE 4

| Example | 17 | 18 | 19 |
|---|---|---|---|
| Retaining time at −20° C. | 0 hour | 1 hour | 5 hours |
| 25% compression hardness (N) | 1.78 (±0.154) | 1.71 (±0.181) | 1.62 (±0.117) |

As shown by Examples 17 to 19, when the cooling time from −1° C. to −20° C. is 6 hours and 20 minutes, i.e., the frozen state is maintained for a prescribed period of time in the production method of the present invention, porous materials having equivalent strength are obtained irrespective of the retaining time at −20° C.

Example 20

Figure 33:
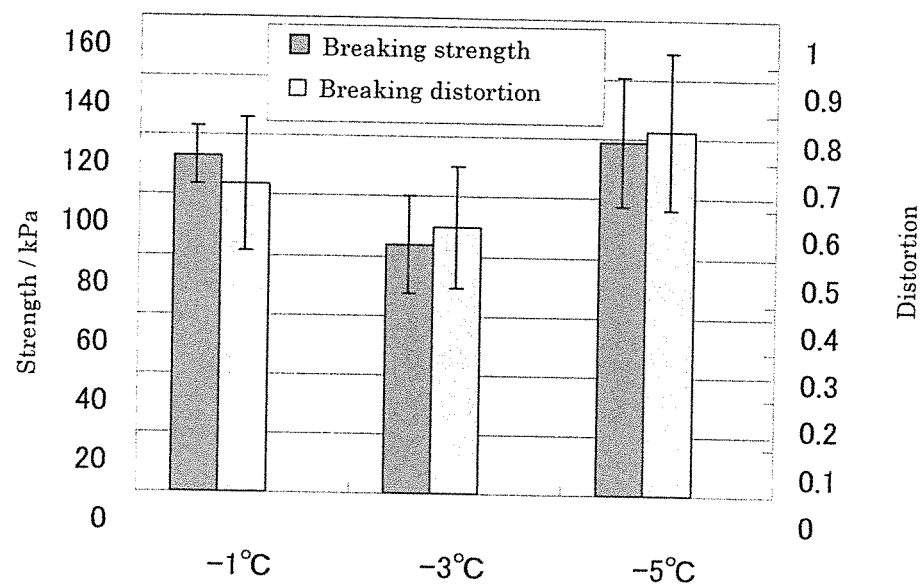
FIG. 33 The figure is a graph showing the mechanical characteristics of porous silk fibroin materials produced in Examples 20 to 22.

A porous silk fibroin material was produced in the same manner as in Example 1 except that acetic acid was used instead of formic acid, a mold having an inner dimension of 80 mm×40 mm×10 mm produced with aluminum plate was used, and the freezing condition was changed as follows. Acetic acid was removed from the resulting porous material in the same manner as described in Example 1, and the porous material was evaluated for mechanical characteristics. The tensile strength (i.e., the maximum breaking strength) and the maximum breaking distortion (i.e., the elongation) of the resulting porous material are shown in FIG. 33 (the left ordinate indicates the maximum breaking strength, and the right ordinate indicates the maximum breaking distortion (i.e., the elongation) and Table 5.

The measurement result was an average value (±standard deviation) of measurement results of 10 positions, which included arbitrary 5 positions of the porous material produced and arbitrary 5 positions of the porous material produced on another day.

Figure 34:
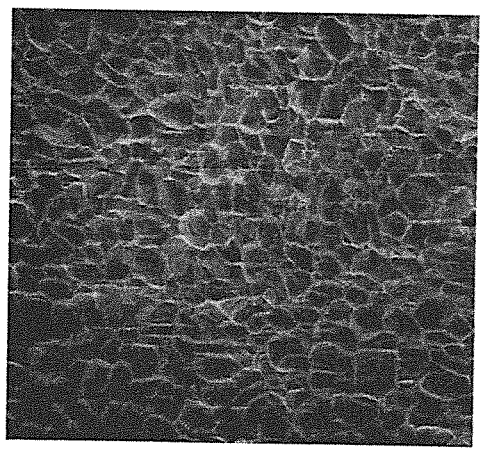
FIG. 34 The figure is a scanning electron micrograph showing an cross section of a porous silk fibroin material produced in Example 20.

The scanning electron micrograph of the cross section of the porous silk fibroin material is shown in FIG. 34.

Freezing Condition

Freezing was performed in the following manner. The silk fibroin solution in the mold was placed in the low temperature thermostat chamber, which had been cooled to −1° C. in advance, and maintained for 2 hours. Thereafter, the solution was cooled until the interior of the chamber reached −20° C. at a cooling rate of 3° C. per hour over 6 hours and 20 minutes, and then maintained at −20° C. for 5 hours.

Example 21

Figure 35:
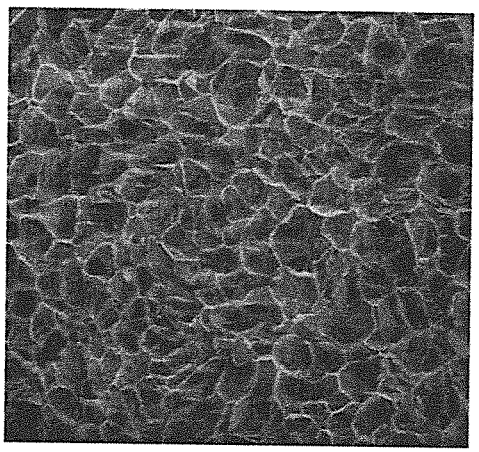
FIG. 35 The figure is a scanning electron micrograph showing an cross section of a porous silk fibroin material produced in Example 21.

A porous silk fibroin material was produced in the same manner as in Example 20 except that the temperature, to which the low temperature thermostat chamber had been cooled in advance, was changed from −1° C. to −3° C. (and the period of time of cooling to −20° C. was changed to 5 hours and 40 minutes). The mechanical characteristics of the resulting porous material are shown in FIG. 33 and Table 5. The scanning electron micrograph of the cross section of the porous silk fibroin material is shown in FIG. 35.

Example 22

Figure 36:
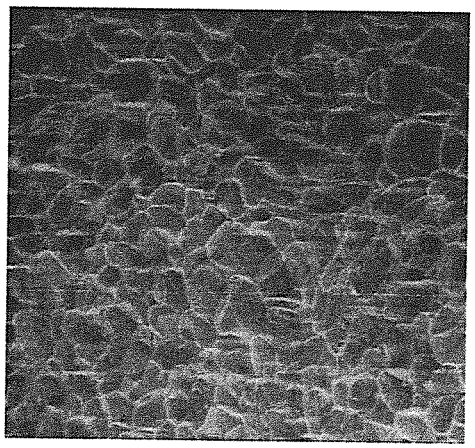
FIG. 36 The figure is a scanning electron micrograph showing an cross section of a porous silk fibroin material produced in Example 22.

A porous silk fibroin material was produced in the same manner as in Example 20 except that the temperature, to which the low temperature thermostat chamber had been cooled in advance, was changed from −1° C. to −5° C. (and the period of time of cooling to −20° C. was changed to 5 hours). The mechanical characteristics of the resulting porous material are shown in FIG. 33 and Table 5. The scanning electron micrograph of the cross section of the porous silk fibroin material is shown in FIG. 36.

TABLE 5

| Example | 20 | 21 | 22 |
|---|---|---|---|
| Pre-cooling temperature (° C.) | −1 | −3 | −5 |
| Breaking strength (kPa) | 113.2 (±9.62) | 83.9 (±16.56) | 118.9 (±21.68) |
| Breaking distortion | 0.648 (±0.138) | 0.561 (±0.129) | 0.765 (±0.166) |

As shown by Examples 20 to 22, when the cooling temperature before freezing is a temperature achieving a supercooling state (i.e., the supercooling temperature), of about −1° C. to −5° C., in the production method of the present invention, porous materials having equivalent strength are obtained.

INDUSTRIAL APPLICABILITY

The porous silk fibroin material produced by the production method of the present invention has high safety and has excellent mechanical characteristics. Accordingly the porous material may be applied to a medical field and a field where the porous material is applied to human body. Specifically, the porous material may be applied widely to a cosmetic and beauty treatment field and the like, and is considerably useful as a face mask that follows the shape of the face.

Furthermore, the porous material may be applied to various fields in industries, for example, a medical field, such as a wound coverage, a pharmaceutical sustained-release carrier and a hemostatic sponge, daily goods, such as a disposable diaper and a sanitary napkin, a cell culture substrate and a tissue regeneration substrate in tissue engineering and regeneration medical engineering, and a support as a habitat of microorganisms and bacteria in a field of water purification and environmental protection.

The invention claimed is:

1. A method for producing a porous silk fibroin material, comprising steps of:
    freezing a silk fibroin solution containing a silk fibroin aqueous solution having an aliphatic carboxylic acid added thereto, without gelling the silk fibroin; and then melting the frozen solution, thereby providing a porous material.

2. The method for producing a porous silk fibroin material according to claim 1, wherein the method further comprises a step of removing the aliphatic carboxylic acid by immersing the porous material obtained after melting in pure water, or a step of removing the aliphatic carboxylic acid by freeze-drying the porous material.

3. The method for producing a porous silk fibroin material according to claim 1, wherein the silk fibroin solution having an aliphatic carboxylic acid added thereto is maintained in a supercooled state for a prescribed period of time before freezing.

4. The method for producing a porous silk fibroin material according to claim 1, wherein an amount of the aliphatic carboxylic acid added is from 0.01 to 18.0% by mass in the silk fibroin solution.

5. The method for producing a porous silk fibroin material according to claim 1, wherein a concentration of the silk fibroin is from 0.1 to 40% by mass in the silk fibroin solution having an aliphatic carboxylic acid added thereto.

6. The method for producing a porous silk fibroin material according to claim 1, wherein the aliphatic carboxylic acid is at least one selected from the group consisting of saturated or unsaturated, monocarboxylic, dicarboxylic or tricarboxylic acids having from 1 to 6 carbon atoms.

7. The method for producing a porous silk fibroin material according to claim 6, wherein the aliphatic carboxylic acid is at least one selected from the group consisting of formic acid, acetic acid, propionic acid, butyric acid, succinic acid, lactic acid, acrylic acid, 2-butenoic acid and 3-butenoic acid.

8. The method for producing a porous silk fibroin material according to claim 2, wherein the silk fibroin solution having an aliphatic carboxylic acid added thereto is maintained in a supercooled state for a prescribed period of time before freezing.

9. The method for producing a porous silk fibroin material according to claim 8, wherein the aliphatic carboxylic acid is at least one selected from the group consisting of saturated or unsaturated, monocarboxylic, dicarboxylic or tricarboxylic acids having from 1 to 6 carbon atoms.

10. The method for producing a porous silk fibroin material according to claim 8, wherein an amount of the aliphatic carboxylic acid added is from 0.01 to 18.0% by mass in the silk fibroin solution.

11. The method for producing a porous silk fibroin material according to claim 8, wherein a concentration of the silk fibroin is from 0.1 to 40% by mass in the silk fibroin solution having an aliphatic carboxylic acid added thereto.

12. The method for producing a porous silk fibroin material according to claim 3, wherein the aliphatic carboxylic acid is at least one selected from the group consisting of saturated or unsaturated, monocarboxylic, dicarboxylic or tricarboxylic acids having from 1 to 6 carbon atoms.

13. The method for producing a porous silk fibroin material according to claim 3, wherein an amount of the aliphatic carboxylic acid added is from 0.01 to 18.0% by mass in the silk fibroin solution.

\* \* \* \* \*